United States Patent [19]

Moaddeb et al.

[11] Patent Number: 5,645,580
[45] Date of Patent: Jul. 8, 1997

[54] IMPLANTABLE MEDICAL DEVICE LEAD ASSEMBLY HAVING HIGH EFFICIENCY, FLEXIBLE ELECTRODE HEAD

[75] Inventors: Shawn Moaddeb, West Hills; John R. Helland, Saugus, both of Calif.

[73] Assignee: Pacesetter, Inc., Sylmar, Calif.

[21] Appl. No.: 278,345

[22] Filed: Jul. 21, 1994

Related U.S. Application Data

[63] Continuation of Ser. No. 984,753, Dec. 3, 1992, abandoned.

[51] Int. Cl.$^6$ .................................................. A61N 1/05
[52] U.S. Cl. ................................................... 607/122
[58] Field of Search ................................. 607/119, 120, 607/122, 123, 121; 128/642

[56] References Cited

U.S. PATENT DOCUMENTS

| | | | |
|---|---|---|---|
| 3,911,928 | 10/1975 | Lagergren | 128/418 |
| 3,935,864 | 2/1976 | Lagergren | 128/418 |
| 4,409,994 | 10/1983 | Doring | 607/126 |
| 4,444,206 | 4/1984 | Gold | 128/784 |
| 4,502,492 | 3/1985 | Bornzin | 607/126 |
| 4,506,680 | 3/1985 | Stokes | 607/126 |
| 4,844,099 | 7/1989 | Skalsky et al. | 607/126 |
| 5,143,089 | 9/1992 | Alt | 607/121 |
| B1 3,911,928 | 11/1988 | Lagergren | 128/786 |
| B1 3,935,864 | 11/1988 | Lagergren | 128/786 |

*Primary Examiner*—William E. Kamm
*Assistant Examiner*—Scott M. Getzow

[57] ABSTRACT

An implantable medical device lead assembly has an electrode head including a flexible tip of elastomeric material embedding at least one rigid or flexible electrode. The at least one electrode and the elastomeric material define a curved tip surface adapted to contact the tissue to be stimulated. The compliance of the tip surface preferably approaches that of the body tissue to be stimulated so as to minimize the stress applied to the heart thereby reducing the adverse reaction of the heart to the presence of the electrode head. By way of example, the at least one electrode may take the form of a metallic or conductive polymer pin or may be made of wire. The elastomeric material may take the form of an envelope disposed about the electrode head and having formed integrally therewith anchoring means preferably comprising a plurality of pliant tines.

42 Claims, 4 Drawing Sheets

IMPLANTABLE MEDICAL DEVICE LEAD ASSEMBLY HAVING HIGH EFFICIENCY, FLEXIBLE ELECTRODE HEAD

This is a continuation of application Ser. No. 07/984,753, filed on Dec. 3, 1992, now abandoned.

FIELD OF THE INVENTION

The present invention relates generally to implantable medical devices for providing stimulating pulses to selected body tissue, and more particularly, to the structure of the electrode head at the distal end of the lead assemblies connecting such devices with the tissue to be stimulated.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. The appended claims are not intended to be limited, however, to any specific example or embodiment described herein.

Pacemaker leads form the electrical connection between the cardiac pacemaker pulse generator and the heart tissue which is to be stimulated. For example, endocardial type leads, that is, leads which are inserted into a vein and guided therethrough into a cavity of the heart, include at their distal end an electrode head having a tip designed to contact the endocardium, the tissue lining the inside of the heart. As is well known, the leads connecting such pacemakers with the heart may be used for pacing; or for sensing electrical signals produced by the heart; or for both pacing and sensing in which case a single lead serves as a bidirectional pulse transmission link between the pacemaker and the heart.

One type of existing implantable pacing lead assembly includes an electrode head having an activated vitreous carbon tip forming the conductive region or stimulation surface maintained in contact with the heart tissue to be stimulated. As is well known, vitreous carbon electrode tips, as well as other electrode tip materials in present use, have several advantages. They can provide relatively low chronic pacing thresholds, improved sensing characteristics and lower polarization voltages. On the other hand, existing electrode tips are relatively rigid, that is, they are substantially less compliant than the heart tissue with which they are in contact. Accordingly, such electrode tips subject the heart tissue to relatively high levels of mechanical stress or pressure concentration which, because of relative movement between the compliant tissue of the beating heart and the noncompliant electrode tip, results in trauma and inflammatory tissue reaction. Among other undesirable consequences, this adverse reaction results in an increase in the stimulation threshold of the heart.

Thus, it is one object of the present invention to provide an implantable medical device lead assembly having an electrode head with structural characteristics minimizing the induced stress on the endocardium and therefore the adverse reaction by the heart to the presence of the electrode head.

To prevent displacement or dislodgement of the electrode head and to maintain the necessary stable electrical contact between the lead tip and the endocardial tissue, the electrode head must be firmly anchored. To achieve this, the electrode head of existing leads includes pliant, rearwardly projecting anchoring means, such as fins or tines, for secure positioning of the electrode head. These fixation elements become anchored in the heart's trabecular network and reduce the incidence of electrode head displacement or dislodgement. In this fashion, the position of the electrode tip is mechanically stabilized, that is, the tip is positively anchored so as to remain in place during the lifetime of the implant. However, although the flexible fixation elements tend to fold down against the outer surface of the lead assembly during its insertion in the vein, these elements nevertheless continue to project to some extent thereby causing resistance to the advancement of the lead assembly within the vein.

Accordingly, another object of the present invention is to reduce the frontal area of the electrode head during implantation and thereby reduce the resistance to advancement of the lead within the vein.

SUMMARY OF THE INVENTION

In accordance with one exemplary embodiment of the present invention, there is provided an implantable lead assembly having a proximal end adapted to be connected to a pulse generator, a distal end having an electrode head including a tip for transmitting electrical pulses to the tissue to be stimulated, and an electrical conductor connecting the proximal and distal ends. The electrode head includes a conductive base having a proximal end connected to the electrical conductor and a distal end coupled to at least one electrode having a tissue-contacting surface. The at least one electrode is embedded in a flexible elastomeric tip so as to define with the tissue-contacting surface of the electrode a tip surface adapted to contact the body tissue to be stimulated. The responsive flexing of the elastomeric tip with each heartbeat causes less stress on the heart tissue and accordingly reduces the extent of the adverse reaction to the heart tissue near the electrode compared to that resulting from a lead with a stiff, conventional tip design. To minimize the induced stress on the heart, the stiffness of the elastomeric tip, at least for small deformations, is designed to be quite low, preferably approaching that of the heart tissue contacted by the tip surface.

In accordance with other aspects of the invention, the elastomeric tip and the tissue-contacting surface of the at least one electrode together define a curved tip surface for making contact with the tissue to be stimulated, and the at least one electrode may furthermore have a variety of cross-sectional configurations including but not limited to circular, square, rectangular, triangular or annular. Still further, to enhance the flexibility of the electrode tip, the at least one electrode itself may be flexible. In this connection, the at least one electrode may be formed of straight, coiled or braided flexible wire or may be fabricated of an electrically conductive polymer.

Pursuant to yet another aspect of the invention, the elastomeric tip may be formed integrally with and as part of an elastomeric sheath or envelope enclosing the electrode head (except for the tissue-contacting surface of the at least one electrode) in which case the envelope may be molded as a single piece in situ about the electrode(s) and electrode base. Alternatively, the envelope may be prefabricated and slipped over the electrode head as a separate step in the manufacture of the lead assembly.

In accordance with still another aspect of the invention, formed integrally with the envelope are a plurality of pliant, rearwardly projecting anchoring tines which, during implantation, fold against the outer surface of the envelope as the electrode head is advanced within the vein toward the heart. The portion of the surface of the envelope so engaged by the tines during implantation is recessed so as to have a smaller outer diameter than the remainder of the envelope. The tines are thus received within the recessed portion of the sleeve so as to be substantially flush with the outer surface of the sleeve. As a result of the reduced frontal area of the electrode head, resistance to advancement of the lead within the vein during implantation is decreased.

BRIEF DESCRIPTION OF THE DRAWINGS

Further objects, advantages and features of the invention will become apparent from the Detailed Description of the Preferred Embodiments when read in conjunction with the accompanying drawings, in which.

DETAILED DESCRIPTION OF THE PREFERRED EMBODIMENTS

The following description presents several preferred embodiments representing the best mode contemplated for practicing the invention. This description is not to be taken in a limiting sense but is made merely for the purpose of describing, with reference to specific examples, the general principles of the invention whose scope is defined by the appended claims.

Figure 1:
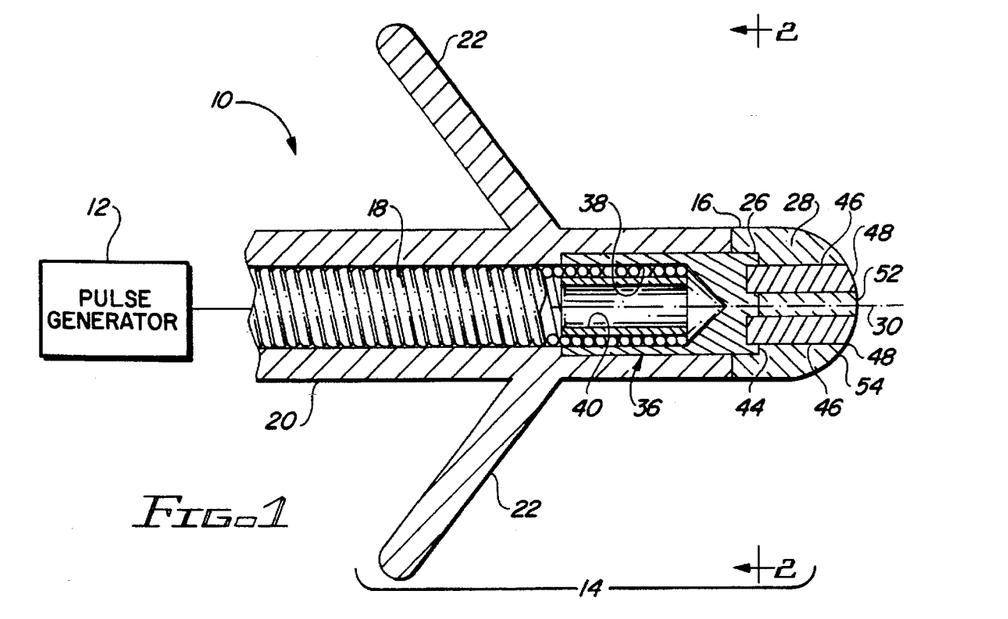
FIG. 1 is a longitudinal cross-section of a lead assembly having an electrode head in accordance with a first embodiment of the present invention.
Figures 2, 4, 5:
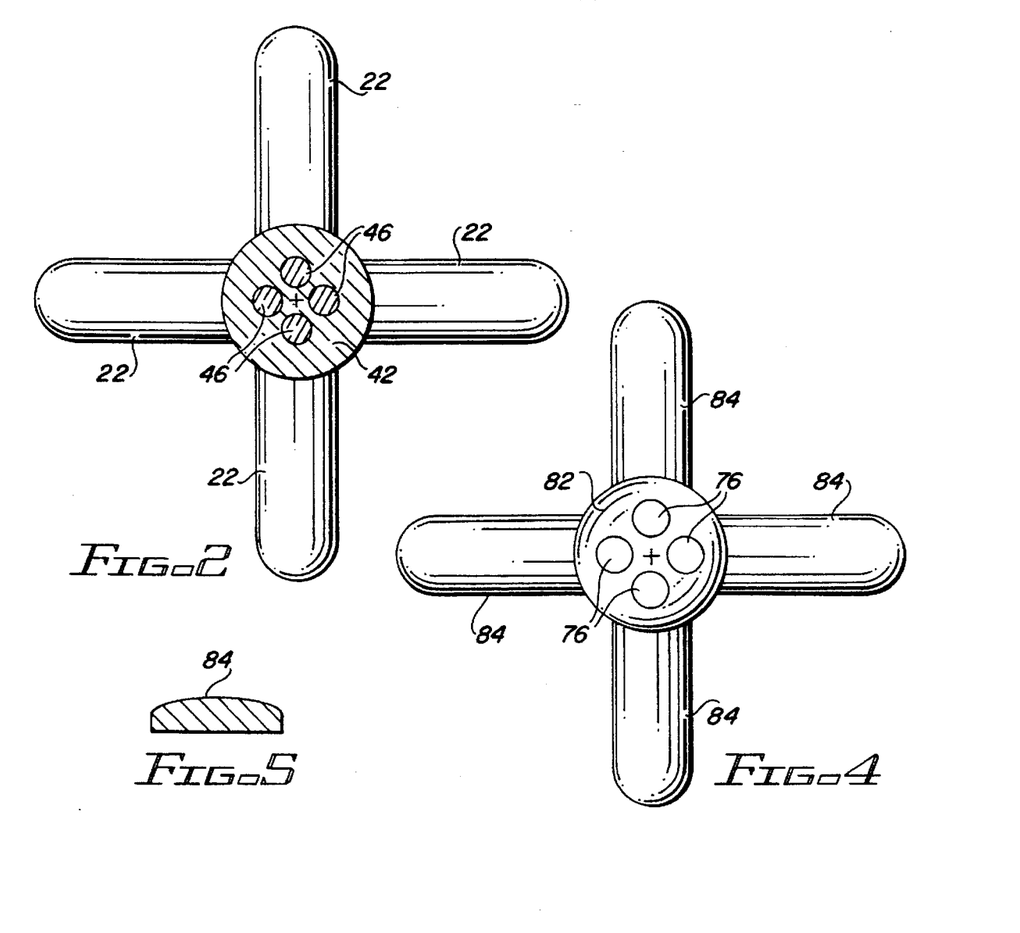
FIG. 2 is a transverse cross-section of the assembly shown in FIG. 1, as seen along the line 2—2.
FIG. 4 is an end view of the electrode head shown in FIG. 3.
FIG. 5 is a cross-section view of an anchoring tine forming part of the electrode head of the second embodiment, taken along the line 5—5 in FIG. 3.

FIGS. 1 and 2 show a flexible pacing lead assembly 10 in accordance with a first preferred embodiment of the invention. The lead assembly 10 includes a proximal end adapted to be connected to a pulse generator 12, a distal end 14 including an electrode head 16, and a coiled conductor 18 for transmitting electrical pulses between the pulse generator 12 and the electrode head 16. The pulse generator 12 may form part of a cardiac pacemaker although, as already indicated, the invention is applicable to a variety of implantable medical devices using pulse generators to stimulate selected body tissue. Further, where both pacing and sensing functions are performed by the lead assembly, the coiled conductor 18 provides a bidirectional electrical transmission link between the electrode head and pulse generator. The assembly 10 further includes an insulating sheath 20 of some suitable material such as silicone rubber or polyurethane, for example, extending substantially the entire length of the lead assembly 10. The sheath 20 includes at the distal end 14 of the lead assembly a plurality of rearwardly projecting pliant tines 22 functioning, as is well known in the art, to interlock in the trabeculae within the heart and thereby prevent displacement of the distal end 14 once implanted. Although tines are the preferred anchoring means for purposes of the present invention, it will be understood by those skilled in the art that fins or some other suitable means may be used instead.

The electrode head 16 includes a generally cylindrical base 26 of conductive implantable material such as a 90/10 alloy of platinum and iridium. The electrode head 26 further includes a flexible tip 28 to be described in greater detail below.

The base 26 has a central, longitudinal axis 30 and a main portion 36 including a bore 38 for receiving the distal end of the coiled conductor 18. The distal end of the coiled conductor 18 is crimped between the wall of the bore 38 and a crimp tube 40 within the distal end of the conductor 18 so as to provide a secure electrical connection between the conductor 18 and the base 26. The main portion 36 of the base 26 includes a transverse surface 44. Press fit in, or otherwise secured to, the base 26 and projecting from the wall 44 are a plurality of parallel, longitudinally extending electrodes 46 in the form of pins disposed about the longitudinal axis 30. The pins 46 may be fabricated of any implantable, conductive material, for example, a 90/10 platinum/ iridium alloy. As an alternative to metal, the pins 46 may be fabricated of an electrically conductive ceramic, oxide or polymer, the latter enhancing the flexibility of the tip 28. In the embodiment under consideration, four electrode pins 46 are utilized but it will be evident that a greater number of pins (for example, five or six) or fewer pins (for example, one or two) may be employed. Preferably, the electrode pins 46 are disposed symmetrically about the longitudinal axis 30. Thus, where four such pins are used they are disposed at 90° intervals and equidistant from the axis 30, as best seen in FIG. 2. Furthermore, although the electrode pins 46 illustrated in FIGS. 1 and 2 have circular cross-sections, it will be evident that other cross-sectional configurations such as triangular, hexagonal, rectangular and annular may be employed. As shown in FIG. 1, the electrode pins 46 extend beyond the distal end of the base 26, terminating at tissue contacting end surfaces 48.

Further in accordance with the present invention, the tip 28 of the electrode head 24 comprises an extremely soft, flexible elastomeric structure molded in situ as a single piece and made of a suitably soft, flexible polymer, for example, silicone rubber elastomer or polyurethane. The polymer completely surrounds or embeds the electrode pins 46 except for their end surfaces 48. The tip 28 is configured to define a curved tip surface 52 and the pin electrode end surfaces 48 are correspondingly curved so as to closely conform to the curvature of the tip surface 52. To reduce polarization voltages, the surface areas of the electrode end surfaces 48 may be increased by techniques known in the art. For example, the end surfaces 48 may be roughened or texturized or otherwise made porous and/or microporous and/or can be coated with such materials as titanium nitride, titanium oxide, iridium oxide, platinum black or carbon. All of these materials are known to increase the true electrical surface area to improve the efficiency of electrical performance by reducing wasteful electrode polarization. Where the tip polymer is a silicone elastomer, this material will include, or can be fabricated to include, dimples, grooves or micropores, or other indentations or recesses in the tip surface 52 for promotion of tissue ingrowth to enhance anchoring the lead tip to the tissue. Such indentations can also be used to house drugs or medications for delivery to the adjoining tissue. In addition, the tip surface 52 may be provided with a lubricous, low friction coating 54, or other coatings of various therapeutic substances including, for example, anti-inflammatory, antiarrhythmic, anti-microbial agents, or other drugs. Still further, the silicone elastomer can be compounded with metal particles or other radio opaque marker material to make the elastomer fluoroscopically visible.

Figure 15:
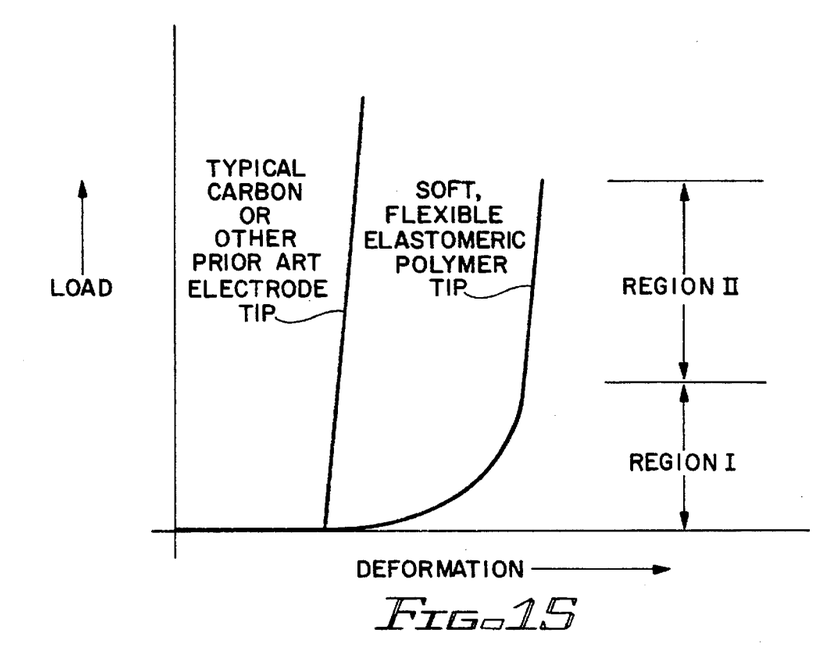
FIG. 15 is a graph comparing the load versus deformation characteristics of a carbon or other stiff electrode tip of the prior art, with those of a combined soft, flexible elastomeric polymer and electrode tip according to the present invention.

Thus, it will be seen that the present invention provides a lead assembly having an electrode head with a flexible polymer tip allowing flexing thereof with each heartbeat to cause less stress on the heart and therefore reduce the adverse reaction of the heart's tissue. Preferably, the stiffness of the polymer tip, at least for small deformations, approaches that of the heart tissue so as to minimize the stress induced by the presence of tip of the electrode head. In this connection, FIG. 15 shows the results of comparative load versus deformation stiffness tests performed on a stiff electrode tip (such as carbon) of the prior art and on a flexible polymer tip in accordance with the invention. The prior art tip is very stiff, the deformation curve thereof having a steep, substantially linear characteristic indicative of a high spring rate. On the other hand, the deformation curve of the polymer tip, when subjected to deforming forces, has two distinct regions-I and II. In region I, for low loads, the polymer controls and the tip exhibits a high degree of compliance, that is, low stiffness. At the beginning of this region, the stiffness or spring rate of the polymer tip is very low and may, for example, be less than 1% that of the prior art tip. As the load and the accompanying deformation increase, the presence of the metal base and electrode pins (where such pins are metal, for example) becomes more evident until, in region II, the metal components begin to control and the slope of the curve starts to parallel that of the stiff prior art tip. To effectively reduce the pressure on the heart tissue by the polymer tip, the stiffness of the tip should be close to that of the heart tissue, at least at the beginning of region I.

Figures 3, 6, 7, 8:
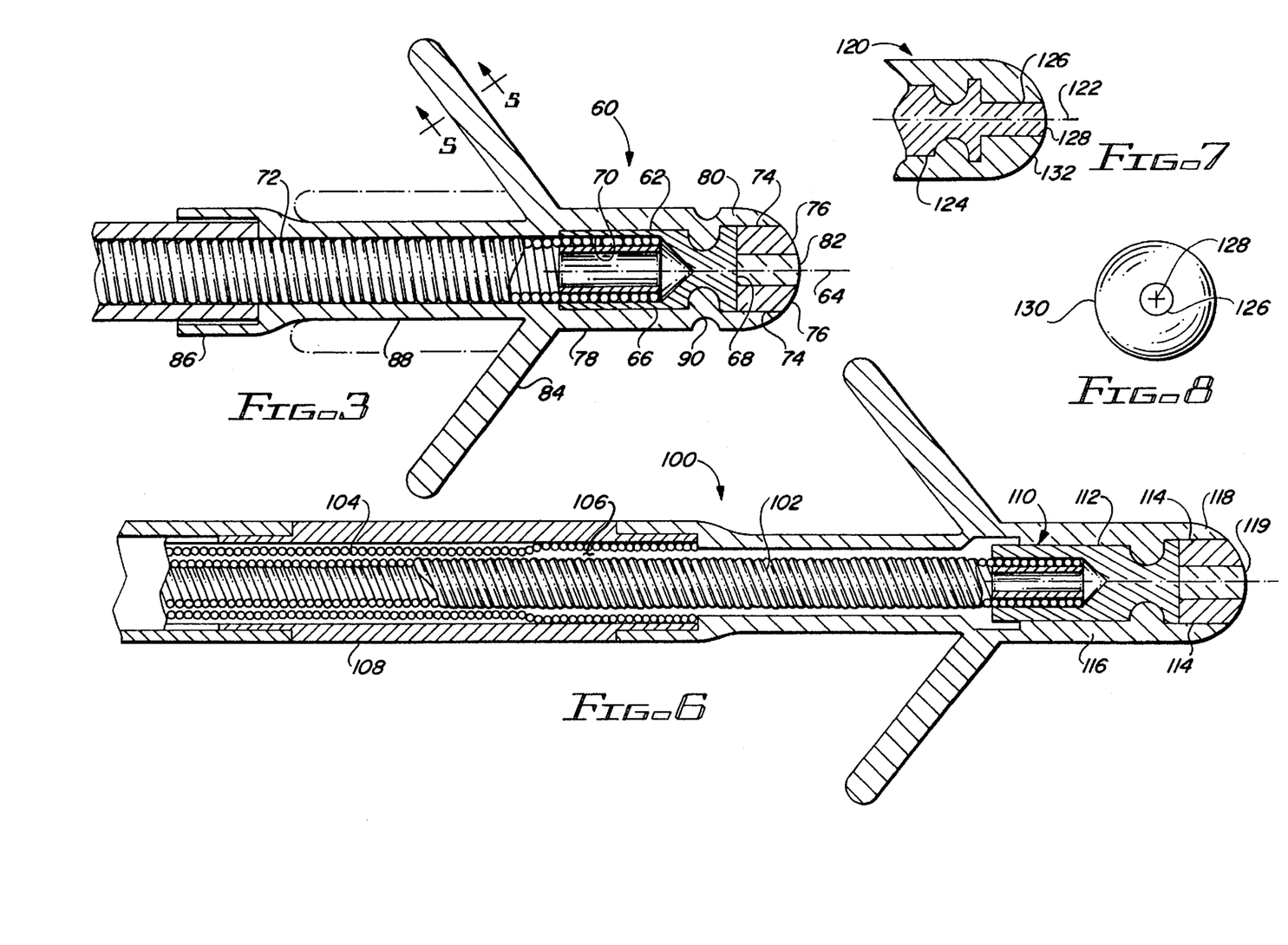
FIG. 3 is a longitudinal cross-section of a lead assembly having an electrode head in accordance with a second embodiment of the invention.
FIG. 6 is a longitudinal cross-section of a lead assembly having an electrode head in accordance with a third embodiment of the invention.
FIG. 7 is a longitudinal cross-section of an electrode head in accordance with a fourth embodiment of the invention.
FIG. 8 is an end view of the electrode head shown in FIG. 7.

Turning now to FIGS. 3–5, there is shown the distal end of a pacing lead assembly including an electrode head 60 illustrating a second preferred embodiment of the invention. The electrode head 60 includes a generally cylindrical, electrically conductive base 62 having a longitudinal central axis 64, a proximal end 66 and a planar, distal end 68. As in the first embodiment, the base may be made of a 90/10 alloy of platinum and iridium or the like and the proximal end 66 includes a bore 70 for receiving the distal end of a coiled conductor 72 for electrically coupling the base 62 to a pulse generator circuit forming part of a cardiac pacemaker. Extending forwardly from the distal end 68 of the base 62 are a plurality of parallel, longitudinally oriented pin electrodes 74. Four such pin electrodes are shown by way of example and each has an end surface 76. The pin electrodes 74 may be made of metal, ceramic, oxides or of a conductive polymer, have a variety of cross-sectional shapes (as already explained) and may be attached to the base in various ways. For example, where the pins are metal, they may be made integral with the base 62 using known precision forming techniques for removing metal. Alternatively, they may be press fit or welded within holes formed in the base 62 or bonded to the base. Except for the end surfaces 76 of the electrode pins 74, the base and the pins 74 are encased within an elastomeric envelope 78 of a very soft and flexible polymer such as silicone rubber elastomer or polyurethane which, according to one alternative, may be molded as a unitary body in situ about the base 62 and pins 74. The polymer envelope 78 and electrode pins 74 define an electrode head tip 80 adjacent the distal end of the base, the tip 80 having a curved outer surface 82. As in the first embodiment, the electrode pin end surfaces 76 are shaped to conform to the curvature of the tip surface 82 and they may be roughened or coated as already explained to increase their surface area. Tines 84 projecting rearwardly from the elastomeric envelope 78 and molded as part thereof serve to anchor the electrode head 60 once in place within a chamber of the heart.

The polymer envelope 78 includes as an integral part thereof a sleeve 86 extending rearwardly from the tines 84 and enclosing the distal end of the coiled conductor 72. During implantation, as the electrode head 60 is advanced within a vein toward the heart, the pliant tines are urged by the wall of the vein to fold down into contact with the outer surface of the sleeve 86. To minimize the frontal area of the electrode head 60 during the implantation procedure and thereby minimize resistance to moving the lead assembly within the vein, the diameter of the portion 88 of the sleeve 86 that is engaged by the folded tines is made smaller than that of the remainder of the envelope 78 to receive the tines in recessed fashion, as shown by the broken lines in FIG. 3. Further in this connection, the height of the tines 84 is preferably minimized by providing the tines with a low profile, convex top, flat bottom cross-section shown in FIG. 5. To enhance anchoring and provide additional positional stability, the base 62 may be necked down and at least one annular groove 90 provided about the envelope 78 just behind the tip 80. Although the fabrication of the envelope 78 as a single piece including the tip 80, the tines and the sleeve 86 is preferred, it will be obvious that the tip 80, for example, may be formed as a separate component. Further, as stated, the envelope 78 may be molded in situ about the electrodes 74, base 62 and conductor 72 or prefabricated in which case the envelope 78 is slipped over the aforementioned components.

The embodiments thus far have been described in terms of a unipolar pacing lead assembly. It should be understood that the invention is applicable as well to bipolar pacing leads having two separate conductors, and to multipolar pacing leads employing multiple conductors. By way of example, FIG. 6 shows how the invention may be applied to a coaxial bipolar lead assembly 100. The assembly 100 includes an inner coiled conductor 102 surrounded by an outer coiled conductor 104. The coils 102 and 104 are electrically isolated from each other by a tubular insulating layer 106 interposed between the coils. The distal end of the outer conductor 104 is electrically connected to a ring electrode 108 having a generally T-shaped cross-section. The distal end of the inner conductor 102 extends beyond the end of the outer conductor 104 and is received by an electrode head 110 substantially identical to the electrode head 60 of the second embodiment. Thus, the electrode head 110 includes a base 112 and pin electrodes 114 all encased within a polymer 116 so as to define a tip 118 having a tissue contacting tip surface 119.

FIGS. 7 and 8 depict yet another embodiment of the present invention in which an electrode head 120 having a longitudinal axis 122 includes an electrically conductive metallic base 124. The base 124 has formed integrally therewith a single, longitudinally extending electrode in the form of a pin 126 centered on the axis 122. As in the embodiments already described, except for a tissue-contacting end surface 128 of the pin electrode 126, the base and pin are embedded in a soft polymer such as polyurethane or silicon rubber so as to define a flexible tip 130 having a curved tip surface 132. All of the features and alternative configurations described in connection with the previous embodiments are applicable to this embodiment.

Figure 9:
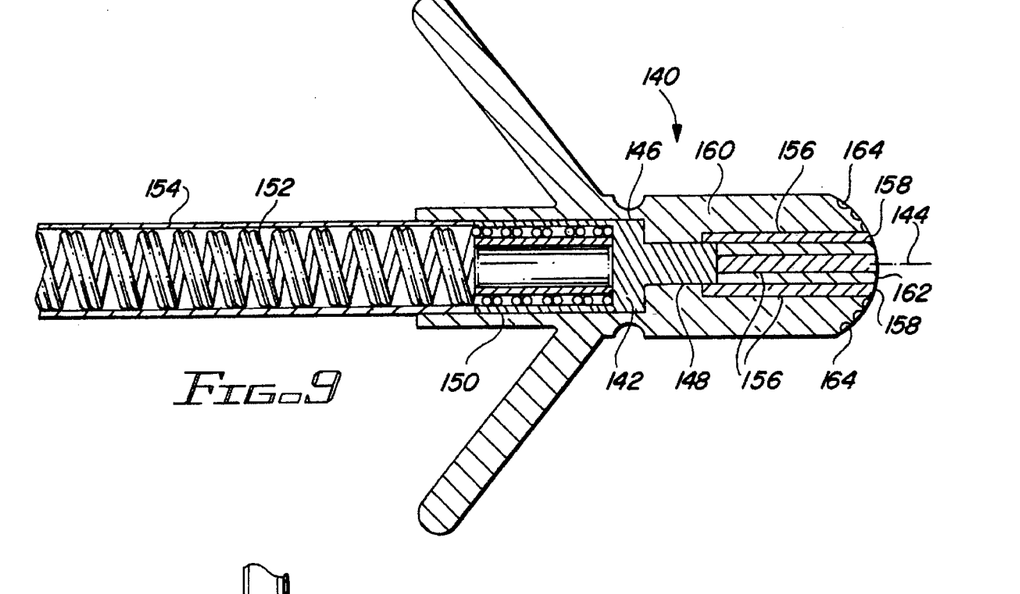
FIG. 9 is a longitudinal cross-section of a lead assembly having an electrode head in accordance with a fifth embodiment of the invention.
Figure 10:
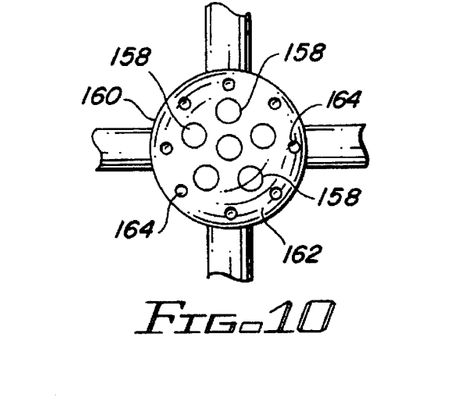
FIG. 10 is an end view of the electrode head shown in FIG. 9.

FIGS. 9 and 10 show an embodiment providing for a substantial increase in the flexibility of the tip of an electrode head 140 further in accordance with the invention. The electrode head 140 includes a generally cylindrical electrically conductive base 142 centered on a longitudinal axis 144. The base 142 includes a main portion 146 and smaller diameter coaxial portions 148 and 150 extending forwardly and rearwardly, respectively, from the main portion 146. A coiled conductor 152 within an outer insulative sheath 154 is securely connected to the rear portion 150 of the base. Projecting forwardly from the front portion 150 of the base substantially parallel with the axis 144 are a plurality of electrodes 156 in the form of small diameter, flexible wires. The flexible wire electrodes 156 are attached to the base portion 150 by laser welding or other means providing a secure electrical and mechanical connection; each wire electrode further has an end surface 158. Any practical number of wire electrodes may be used. For example, seven are shown in the embodiment under consideration. As in the previous examples of the invention, the wire electrodes and base are embedded within a soft elastomeric polymer 160 such as polyurethane or silicone rubber with the wire electrode end surface 158 being exposed to make contact with the tissue to be stimulated. And, as in the previously described embodiments, the portion of the electrode head forwardly of the base 142 and including the wire electrodes 156, defines a tip 160 having, preferably, as before, a tip surface 162 that is curved and to whose curvature the wire electrode ends 158 conform. Alternatively, the wire electrode ends may be heated and melted and then allowed to cool to form either a flat or globular end surface.

It will be appreciated that the flexible wire electrodes enhance the overall flexibility of the tip so as to even further reduce the risk of trauma and resulting adverse tissue reaction of the heart. Instead of the wire electrodes in the form shown in FIGS. 9 and 10, the advantages of this embodiment of the invention may be realized by using a variety of electrode forms providing the desired flexibility. For example, instead of the straight wire electrodes shown in FIGS. 9 and 10, a coil or braid of fine wire can be used in place of each straight wire or, still further, flexible, electrically conductive ribbons may be used instead of wire. The embodiment under consideration may further include pores 164 or other indentations, grooves or recesses in the tip surface 162 for enhancing tissue ingrowth or for use as receptacles for storage of drugs for drug delivery. Such pores typically have a diameter of about 50 microns, but could be used in ranges of 5 to 500 microns. It should be noted that this expedient is equally applicable to the other embodiments described herein.

Figure 11:
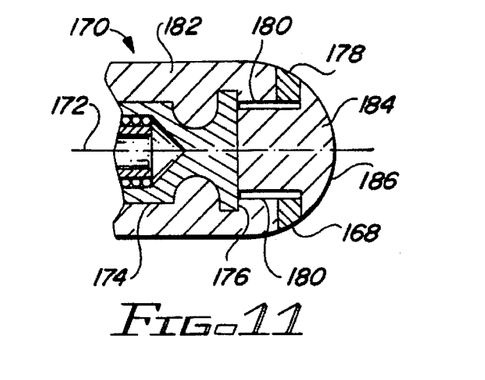
FIG. 11 is a longitudinal cross-section of an electrode head in accordance with a sixth embodiment of the invention.
Figure 12:
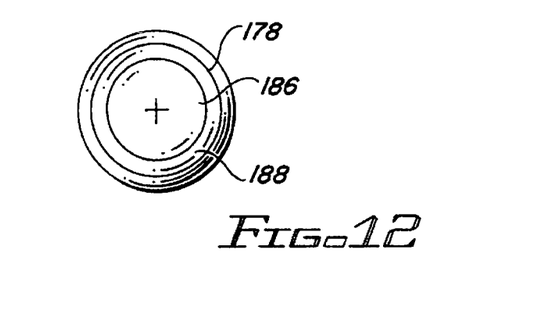
FIG. 12 is an end view of the electrode head shown in FIG. 11.

FIGS. 11 and 12 show yet another embodiment of the invention including a generally cylindrical electrode head 170 having a longitudinal axis 172 and incorporating an electrically conductive base 174. The base 174 has a distal planar surface 176 carrying a ring electrode 178. The ring electrode is electrically and mechanically coupled to the surface 176 of the base by means of flexible wires 180 or the like whose opposite ends are laser welded or otherwise secured to the base and ring electrode. The base and ring electrode are encapsulated within a polymer 182 molded about the electrode head components thereby defining a tip 184 having a curved outer surface 186. The ring electrode is concentric with the longitudinal axis 172 and includes an outer annular tissue-contacting surface 188 curved to conform to the tip surface and to thereby be flush therewith. Instead of a single ring electrode, it will be obvious that multiple ring electrodes may also be employed as an alternative to that shown in FIGS. 11 and 12.

Figure 13:
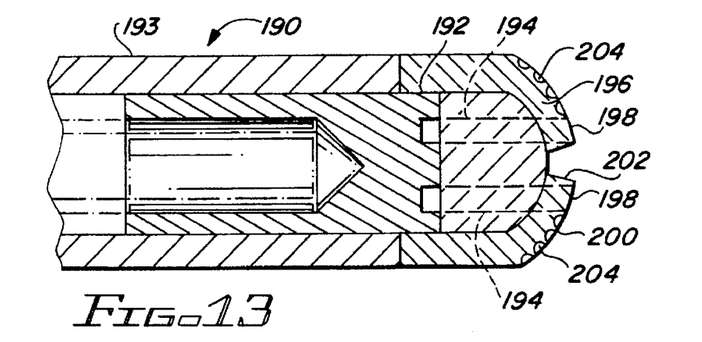
FIG. 13 is a longitudinal cross-section of an electrode head in accordance with a seventh embodiment of the invention.
Figure 14:
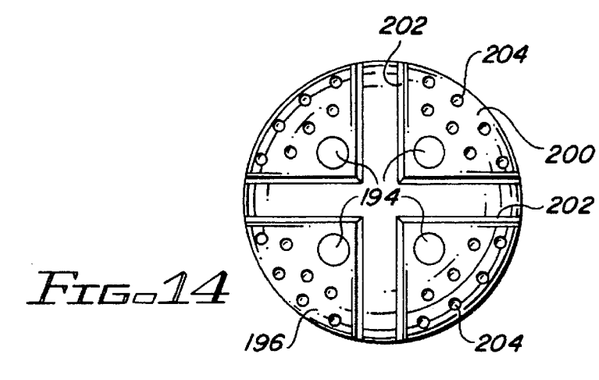
FIG. 14 is an end view of the electrode head shown in FIG. 13.

A seventh embodiment 190 of an electrode head according to the present invention, similar to the first embodiment, is shown in FIGS. 13 and 14. The electrode head 190 includes a base 192, pin electrodes 194 projecting from the base, a polymer sheath 193 about the base 192, and a polymer tip 196 embedding the pins 194 except for their end surfaces 198. The tip 196, as in the preceding embodiments, has a curved outer surface 200 and the configuration of the end surfaces 198 of the pin electrodes conform to the curvature of the tip surface 200. This embodiment further includes intersecting grooves 202 formed in the tip surface 200 to enhance anchoring stability. The tip surface 200 may also include micropores 204 for enhancing tissue ingrowth and, as before, a hypo-inflammatory, antimicrobial coating or other therapeutic coating may be applied to the tip surface 200.

What is claimed is:

1. A lead assembly adapted to transmit electrical signals between an implantable medical device and selected body tissue, the lead assembly having a proximal end and a distal end and an electrode head forming said distal end, the electrode head being a unitary soft flexible elastomeric structure having a tip surface portion for contacting selected body tissue and at least one electrically conductive electrode in electrical communication with the medical device and extending within the electrode head to the tip surface portion thereof for making electrical contact with the selected body tissue; and the electrode head further including anchoring means projecting from the electrode head for anchoring the electrode head to the selected body tissue.

2. A lead assembly as defined in claim 1, in which:

the stiffness of the tip surface portion is approximately the same as that of the selected body tissue.

3. A lead assembly as defined in claim 1, in which:

the at least one electrode is made of metal or conductive ceramic or conductive oxide.

4. A lead assembly as defined in claim 3, in which:

the at least one electrode is in the form of a pin electrode.

5. A lead assembly as defined in claim 1, in which:

the at least one electrode is flexible.

6. A lead assembly as defined in claim 5, in which:

the at least one electrode is in the form of a flexible wire.

7. A lead assembly as defined in claim 6, in which:

the at least one wire electrode has a coiled or braided configuration.

8. A lead assembly as defined in claim 5, in which:

the at least one electrode is fabricated of a conductive polymer.

9. A lead assembly as defined in claim 1, in which:

the electrode head has a longitudinal axis and the at least one electrode has an annular configuration substantially concentric with the longitudinal axis.

10. A lead assembly as defined in claim 1, in which:

said at least one electrode has an end surface and the tip surface portion of the electrode head is curved, the end surface of said at least one electrode conforming to the curvature of the tip surface portion.

11. A lead assembly as defined in claim 10, wherein the end surface of said at least one electrode comprises a roughened end surface.

12. A lead assembly as defined in claim 10, wherein the end surface of said at least one electrode comprises a textured end surface.

13. A lead assembly as defined in claim 10, wherein:

the area of the end surface of said at least one electrode includes a coating of conductive particulate matter.

14. A lead assembly as defined in claim 10, wherein:

the area of the end surface of said at least one electrode includes a coating with a material selected from the group consisting of titanium nitride, titanium oxide, iridium oxide, platinum black and carbon.

15. A lead assembly as defined in claim 1, in which:

the tip surface portion is coated with a therapeutic agent.

16. A lead assembly as defined in claim 1, in which:

the elastomeric portion of the tip surface portion includes recesses.

17. A lead assembly as defined in claim 16, in which:

the recesses contain at least one therapeutic agent for delivery to the selected body tissue.

18. A lead assembly as defined in claim 1, in which:

the tip surface portion includes at least one groove formed therein.

19. A lead assembly as defined in claim 18, in which:

the at least one groove in the tip surface portion contains at least one therapeutic agent for delivery to the selected body tissue.

20. A lead assembly as defined in claim 1, in which:

the electrode head has an outer surface and the anchoring means are adapted to fold against a portion of the outer surface of the electrode head, said portion of said outer surface of said electrode head being recessed to receive the anchoring means whereby the frontal area of the electrode head is reduced.

21. A lead assembly as defined in claim 20, in which:

the anchoring means comprises a plurality of compliant tines formed integrally with the electrode head.

22. A lead assembly as defined in claim 21, in which:

each tine has a cross-section configured to minimize said frontal area.

23. A lead assembly having a proximal end adapted to be connected to an implantable medical device for stimulating selected body tissue comprising heart tissue, a distal end and an electrical conductor connecting said proximal and distal ends, the distal end having an electrode head being a unitary compliant elastomeric structure, the electrode head comprising:

an electrically conductive base having a proximal end coupled to said electrical conductor, and a distal end;

a plurality of electrically conductive electrodes connected to and projecting from the distal end of the base;

the electrode head defining a tip surface adapted to contact the selected body tissue to be stimulated, the tip surface being compliant for flexing under the action of heartbeats for reducing stress on heart tissue; and anchoring means projecting from the electrode head for anchoring the electrode head to the selected body tissue.

24. A lead assembly as defined in claim 23, in which:

the stiffness of the tip surface is approximately equal to that of the selected body tissue to be stimulated.

25. A lead assembly as defined in claim 23, in which:

the electrodes are made of metal or conductive ceramic or conductive oxide.

26. A lead assembly as defined in claim 25, in which:

each electrode is in the form of a pin electrode.

27. A lead assembly as defined in claim 23, in which:

the electrodes are flexible.

28. A lead assembly as defined in claim 27, in which:

each electrode is made of wire.

29. A lead assembly as defined in claim 28, in which:

the wire comprising each electrode is coiled or braided.

30. A lead assembly as defined in claim 27, in which:

each electrode is fabricated of a conductive polymer.

31. A lead assembly as defined in claim 23, in which:

the tip surface of the electrode head is curved; and each of said electrodes has an end surface configured to conform to the curvature of the tip surface.

32. A lead assembly as defined in claim 23, in which:

the electrode head has an outer surface and the anchoring means are adapted to fold against a portion of the outer surface of the electrode head, said portion of said outer surface of said electrode head being recessed to receive the anchoring means whereby the frontal area of the electrode head is reduced.

33. A lead assembly as defined in claim 32, in which:

the anchoring means comprises a plurality of compliant tines formed integrally with the electrode head.

34. A lead assembly as defined in claim 33, in which:

each tine has a cross-section configured to minimize said frontal area.

35. An electrode head adapted to be connected to the distal end of an implantable medical device lead assembly, the electrode head comprising:

an electrically conductive base having a distal end;

at least one electrode connected to and projecting from the distal end of the base; the electrode head being formed of a unitary flexible elastomeric material in which said at least one electrode is embedded and defining therewith a flexible tip surface configured to contact selected body tissue to be stimulated by the implantable medical device, the tip surface flexing in response to relative motion of the body tissue for reducing stress on the body tissue; and anchoring means projecting from the electrode head for anchoring the electrode head to the selected body tissue.

36. An electrode head as defined in claim 35, in which:

the elastomeric material is a soft polymer of polyurethane or silicone elastomer.

37. An electrode head as defined in claim 36, in which:
the stiffness of the tip surface is approximately the same as that of the body tissue.

38. An electrode head as defined in claim 35, in which:
the at least one electrode is made of metal or conductive ceramic or conductive oxide.

39. An electrode head as defined in claim 35, in which:
the at least one electrode is made of a conductive, flexible material.

40. An electrode head as defined in claim 35 in which:
the anchoring means comprises a plurality of compliant tines formed integrally with the electrode head.

41. An electrode head as defined in claim 40, in which:
the electrode head has an outer surface and the tines are adapted to fold against a portion of the outer surface of the electrode head, said portion of said outer portion of said electrode head being recessed to receive the tines whereby the frontal area of the electrode head is reduced.

42. An electrode head as defined in claim 41, in which:
each tine has a cross-section configured to minimize said frontal area.

* * * * *